United States Patent [19]

Scales et al.

[11] Patent Number: 4,476,590
[45] Date of Patent: Oct. 16, 1984

[54] ANTIMICROBIAL SURGICAL IMPLANTS

[75] Inventors: John T. Scales, Stanmore; Michael J. Wilkinson, Radlett, both of England

[73] Assignee: National Research Development Corporation, London, England

[21] Appl. No.: 328,594

[22] PCT Filed: Mar. 26, 1981

[86] PCT No.: PCT/GB81/00058
§ 371 Date: Nov. 23, 1981
§ 102(e) Date: Nov. 23, 1981

[87] PCT Pub. No.: WO81/02667
PCT Pub. Date: Oct. 1, 1981

[30] Foreign Application Priority Data

Mar. 27, 1980 [GB] United Kingdom ............... 8010362
Apr. 3, 1980 [GB] United Kingdom ............... 8011429
Oct. 10, 1980 [GB] United Kingdom ............... 8032768

[51] Int. Cl.³ .............................................. A61F 1/04
[52] U.S. Cl. ................................... 3/1.91; 128/92 C
[58] Field of Search .................. 128/335.5, 155, 156, 128/92 R, 92 A, 92 B, 92 BA, 92 BC, 92 C, 92; 3/1.91, 1 R, 1.911; 604/265

[56] References Cited

U.S. PATENT DOCUMENTS 2,040,806 5/1936 Feigl ................................... 128/155
3,557,795 1/1971 Hirsch ............................. 128/335.5
4,054,139 10/1977 Crossley ............................. 604/265
4,263,681 4/1981 Notton ................................. 3/1.91

FOREIGN PATENT DOCUMENTS 334627 10/1930 United Kingdom .
1582016 12/1980 United Kingdom .
2053687 2/1981 United Kingdom .
1588933 4/1981 United Kingdom .

OTHER PUBLICATIONS

"Prophylaxis of Indwelling Urethral Catheter . . . ", Akiyami et al., J. of Urology, 4-1978, vol. 121.
"An In-Vivo Study of Bacterial Response to Inert and Reactive Metals . . . ", Gristina et al., J. of Biomed Mater. Res., Wiley, vol. 10, pp. 273-281 (1976).

Primary Examiner—Benjamin R. Padgett
Assistant Examiner—T. J. Wallen
Attorney, Agent, or Firm—Cushman, Darby & Cushman

[57] ABSTRACT

Surgical implants, especially endoprosthetic orthopaedic implants and sutures, are rendered antimicrobial by the presence of a bioerodible metallic silver component, especially a surface coating, which provides in vivo a sustained release of silver ions in a concentration sufficient to provide a localized antimicrobial effect but insufficient to cause significant damage to connective tissue. Latently bioerodible silver components of an implant can be activated by, for example, abrasion, heating to above about 180° C. or, especially, contact with hydrogen peroxide.

15 Claims, 11 Drawing Figures

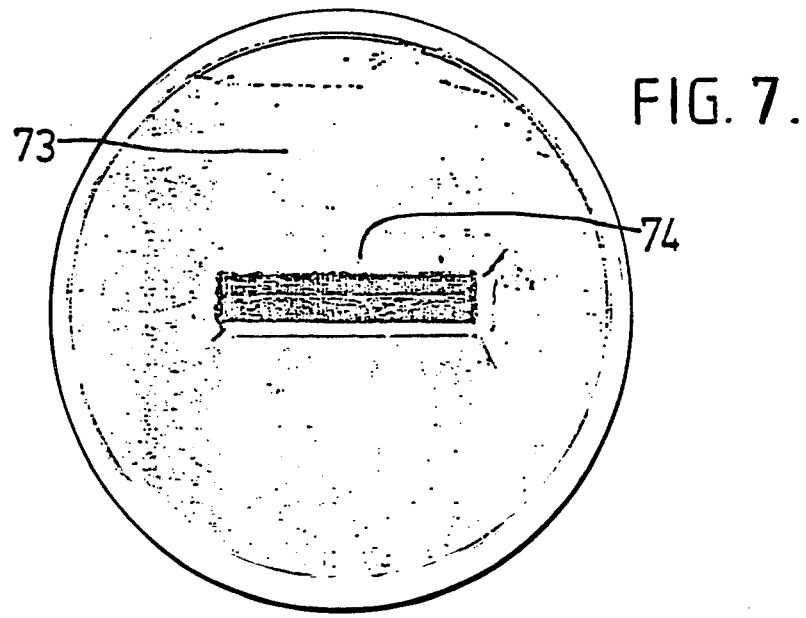
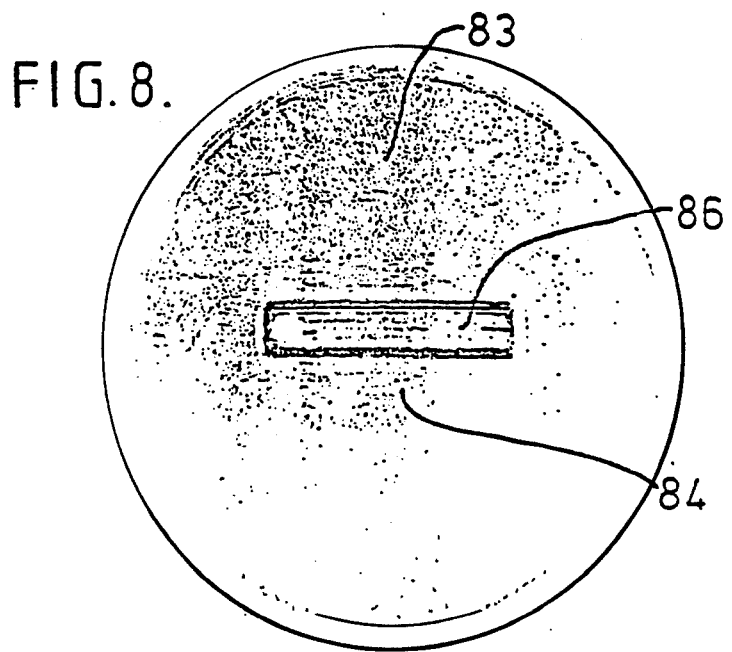

ANTIMICROBIAL SURGICAL IMPLANTS

The present invention relates to endoprosthetic implants for the human or animal body and provides a manner of rendering such implants antimicrobial. The invention has particular, but not exclusive, application to orthopaedic implants.

As used in this Specification (including the claims thereof), the term "endoprosthetic implant" includes the entire implant, parts thereof and fixing means therefor. In particular, said term includes, for example, orthopaedic pins, plates and screws, and artificial joints.

With few exceptions, it has been the established practice for many years to manufacture endoprosthetic implants from materials which induce minimal tissue response and effects and yet possess adequate mechanical properties for the particular application. In the particular case of endoprosthetic orthopaedic implants, structural materials usually have been sought which do not corrode in vivo and which do not cause bone reabsorption.

Materials used for orthopaedic implants have progressed from the early use of common metals and their alloys, especially mild steel, through the use of surgical stainless steel to the present day use of cobalt chromium molybdenum alloys and titanium and titanium alloys. Other materials which are used in endoprosthetic orthopaedic implants include ceramic and carbon-based materials and some synthetic plastics materials such as ultra-high molecular weight polyethylene, some forms of nylon, polymethylmethacrylate and silicone elastomers. None of these materials have fulfilled entirely the aim of bioinertness (i.e. bioinactivity) in all circumstances, but in general the attempt usually has been towards the use of more fully inert materials to prevent as far as possible any interaction in vivo. The search for materials of greater bioinertness for use in surgical implants continues without diminution.

In the early years of implant surgery, silver was employed in the manufacture of endoprosthetic implants. In particular, silver wire, silver plates and silver-plated screws were used in bone repair surgery and tracheotomy tubes were silver plated. However, the use of silver and silver plated implants had generally ceased by about 1935 in the ever continuing search for greater bioinertness for implant materials. In the particular case of orthopaedic implants, silver was and still is, generally considered to be unacceptable as an implant material, because of poor mechanical properties, connective tissue reaction and excessive subperiosteal bone growth (see, for example, Venable et al, Ann. Surg. 105, 917–938, 1937).

Silver was one of the first metals known to man. Silver artifacts have been found in tombs dating to 4,000 B.C. It is believed that in antiquity, silver was deliberately chosen for water receptacles to conserve the quality of drinking water. Silver needles have traditionally been used in acupuncture, which is one of the oldest forms of invasive medical treatment. The antimicrobial properties of silver compounds have been recognized for about 100 years. The first report of silver compounds for pharmaceutical use is that of aqueous silver nitrate for preventing eye infection in new born babies. Since then a range of silver salts, colloids and complexes have been employed to prevent and control infection. Colloidal metallic silver has been used topically for conjunctivitis, urethritis and vaginitis.

The antimicrobial activity of metallic silver has been exploited in filter elements for domestic and industrial use (see Disinfection, Sterilization, and Preservation; Editor S. S. Block, Publishers Lea and Febiger, Philadelphia, 1977). For this purpose, silver has been deposited on porous carbon or used in the form of a wire, gauze or other physical shape. It is believed that the active agent is the silver ion and that impurities must be present in the metal to expedite oxidation and solution.

The body's ability to counter infection in the immediate vicinity of an implant is reduced thereby increasing the risk of a localised infection around the implant. This risk persists beyond the immediate postoperative period and is a significant complication in implant surgery. It is usually difficult to treat such infection. Often additional surgery and sometimes removal of the implant is required in order to effectively treat the infection.

It has been proposed that inorganic silver compounds should be incorporated in bone cement to reduce the risk of postoperative infection following the insertion of an endoprosthetic orthopaedic implant. In particular, J. A. Spadaro et al (Clinical Orthopaedics and Related Research, 143, 266–270, 1979) proposed that low concentrations of inorganic silver compounds should be incorporated in polymethylmethacrylate bone cement for this purpose. The compounds which they evaulated for this purpose were silver chloride (AgCl), silver oxide ($Ag_2O$), silver sulphate ($Ag_2SO_4$), silver phosphate ($Ag_3PO_4$) and chlorided silver (Ag-AgCl). They report that their proposal was based upon the known antibacterial effects of silver ions. The least effective of the compounds evaluated was chlorided silver which at 0.5% concentration did not inhibit any of the three bacteria tested, viz Staphylococcus aureus, Escherichia coli and Pseudomonas aeruginosa. In contrast, each of the other compounds evaluated significantly inhibited the bacteria at 0.5% concentration except for silver chloride which did not inhibit Escherichia coli at that concentration.

It has also been reported by the same workers that electrically generated silver ions constitute a potent broad spectrum antibacterial agent of use as adjunctive treatment in the management of chronic osteomyelitis (Becker et al, J. Bone and Joint Surg., 60A, 871–881, 1978). The silver iontophoresis was used after standard surgical treatment for osteomyelitis, including debridement and the opening of all pockets of infection. When the wound was to be surgically closed, silver wire electrodes were temporarily inserted for a period of about six weeks. Electrical current was applied to the electrode from an external power source.

It is specifically stated in Becker et al (supra) that the clinical utility of silver is limited and, in particular, that diffusion of silver ions from a metallic surface such as silver foil is negligible. This statement is consistent with the absence, to the best of our knowledge, of any reported observation of significant antimicrobial activity when using the prior art silver or silver coated implants. Further, it is consistent with our own tests which have shown that commercially available 99.99% pure silver bar and foil do not inhibit the in vitro growth of Staphylococcus aureus.

Having regard to the above, the present state of the art can be summarized as being that, despite the reported antimicrobial activity of certain forms of metallic silver and its use before about 1935 in surgical implants, the use of metallic silver in endoprosthetic implants is contraindicated. Further, recent developments in the field of orthopaedic surgery teach the use of silver salts and electrically generated silver ions but not metallic silver surfaces for the prophylactic or adjunctive treatment of postoperative infections following implant surgery.

It is the object of the present invention to provide a simple, effective and surgically acceptable manner of rendering endoprosthetic implants antimicrobial to provide a prophylactic treatment of postoperative infection. Surprisingly, it has been found that this object can be achieved by going against the long-established teachings of the art and using metallic (including alloyed) silver, provided that two criteria are met. One criteria is that the metallic silver should be activated in the sense that it erodes in vivo to provide a sustained release of silver ions at a concentration sufficient to produce a localized antimicrobial effect but insufficient to cause significant damage to connective tissue. The other criteria is that the structural material of the implant should be a substantially bioinert material so that the mechanical integrity of the implant is retained despite the erosion of the metallic silver.

According to one aspect of the present invention, there is provided an endoprosthetic implant comprising a permanent implant structure formed of a substantially bioinert structural material providing permanent mechanical integrity to the implant, wherein a bioerodible metallic silver component is deposited in or on said permanent implant structure and provides in vivo a sustained release of silver ions in a concentration sufficient to provide a localized antimicrobial effect but insufficient to cause significant damage to connective tissue.

In another aspect of the present invention, there is provided a method of rendering antimicrobial an endoprosthetic implant comprising a permanent implant structure formed of a substantially bioinert structural material providing permanent mechanical integrity to the implant structure, said method comprising depositing on or in said implant a quantity of bioerodible metallic silver which will provide in vivo a sustained release of silver ions in a concentration sufficient to provide a localized antimicrobial effect but insufficient to cause significant damage to connective tissue.

In a further aspect of the present invention, there is provided a method of rendering antimicrobial an endoprosthetic implant comprising a permanent implant structure formed of a substantially bioinert structural material providing permanent mechanical integrity to the implant and a latently bioerodible metallic silver component deposited in or on the permanent implant structure, said method comprising treating said implant to render said silver component bioerodible to provide in vivo a sustained release of silver ions in a concentration sufficient to provide a localized antimicrobial effect but insufficient to cause significant damage to connective tissue.

In yet another aspect of the present invention, there is provided a method of prophylactic treatment of postoperative infection following endoprosthetic implant surgery, said method comprising selecting an endoprosthetic implant comprising a permanent implant structure formed of a substantially bioinert structural material providing permanent mechanical integrity to the implant and a latently bioerodible metallic silver component deposited in or on the permanent implant structure, treating said selected insert to render the metallic silver component thereof bioerodible to provide in vivo a sustained release of silver ions in a concentration sufficient to provide a localized antimicrobial effect but insufficient to cause significant damage to connective tissue, and surgically implanting the thus activated implant in the human or animal body.

As mentioned previously, the invention has particular, but not exclusive, application to endoprosthetic orthopaedic implants. However, the invention is applicable to any endoprosthetic implant structure which has permanent structural integrity. The implant can be made of any structural material which is substantially bioinert but usually will be made of titanium or titanium alloy, or cobalt chrome molybdenum alloy, or ceramic material, or non-toxic synthetic plastics material, or any combination of these materials. Examples of implants to which the invention has particular application include orthopaedic plates, pins and screws and, artificial joints.

The metallic silver component can be made of commercially pure (i.e. 99.99%) silver metal or of a silver alloy, for example a dental amalgam or silver solder. In order to promote galvanic action producing silver ions, there can be used an alloy of silver with a more noble metal such as gold or platinum.

The silver component will be deposited in or on the permanent implant structure. Conveniently, the silver component is constituted by a surface coating on at least part of the implant structure. However, the component can be constituted in other ways, for example as a deposit in one or more cavities provided in the permanent implant structure or as a permeant in a porous substrate in or on the permanent implant structure.

The location of the silver component in the implant will be selected having regard to the structure and intended application of the implant. In the case of a silver coating, said coating can extend over all or only a selected part or parts of the implant structure. Similarly, in the case of cavity-deposited silver or permanent silver, the silver can be distributed over the implant structure or provided only at a selected part or parts thereof.

The quantity of silver in the composite implant and the rate of erosion in vivo is such as to provide a sustained release of silver ions in sufficient concentration to produce a localized antimicrobial effect but insufficient to produce significant damage to connective tissue. The required concentration balance readily can be achieved because antimicrobial activity is provided at a concentration of the order of nanogrammes/ml whereas connective tissue damage appears to require concentrations of six orders higher, i.e. milligrammes/ml. Nevertheless, the cumulative effects of sustained release of silver ions in the body must be considered when determining the quantity of silver to be used and the rate of erosion to avoid toxic effects in the human or animal body. Any osteogenesis produced by the antimicrobial concentrations of silver can be tolerated and in many cases actually can be advantageous in that, for example, an orthopaedic implant is more securely located and/or the bone thickened in an area of weakness where it is joined to the implant.

It has been found that the quantity of silver in the composite implant suitably is the amount corresponding to a surface coating of 10 to 1000 Angstroms applied over the entire surface of the implant. This corresponds in the case of a large implant such as an artificial hip joint to not more than about 2 mg silver with proportionally smaller amounts of silver for smaller implants. Usually, an amount corresponding to such a coating of 25 to 500 Angstroms thick will be used.

It is an essential feature of the invention that the metallic silver component should be bioerodible to provide in vivo the silver ions required for the desired antimicrobial activity. As previously stated, metallic silver surfaces such as silver bar, silver foil and silver coatings applied by conventional plating techniques are not significantly antimicrobial or at least lose any antimicrobial activity shortly after manufacture. Moreover, the preoperative treatment of surgical implants at the time when silver or silver-plated implants were in use was such that the silver content of said implants would not have been suitably activated to become antimicrobial. In particular, sterilization would have been conducted using temperatures of no more than about 100° C. and/or sterilizing agents, such as alcohol, which do not activate the silver content to bioerode. However, there are a number of ways in which metallic silver can be rendered suitably bioerodible, including chemical, mechanical and/or thermal treatment as discussed below. It is expected that treatments additional to those discussed below will be apparent to those skilled in the metallurgical art.

An existing metallic silver surface can be activated by abrasion to freshly expose the metal surface. For example, the surface can be scratched with one or more pointed tools or, more usually, rubbed with an abrasive material or tool. In a particular embodiment of the invention in which the implant is an artificial joint, the silver component can comprise a coating on or deposit at a wear surface of the joint so that movement of the joint continually abrades the silver coating or deposit. In another embodiment, the silver is deposited in or on a substrate of a more readily bioerodible material, for example iron, so that silver is released as the substrate erodes.

An existing metallic silver surface also can be activated thermally by heating to a temperature in excess of about 180° C. The duration of heating required to activate the surface will depend upon the temperature and the nature of the surface. Usually a temperature in the range 200° to 270° C. will be used for a period of 16 to 60 mins. It has been found surprisingly that the surface is activated either in a molecular oxygen-containing atmosphere such as gaseous oxygen or air, or in an inert atmosphere, such as gaseous argon or nitrogen.

The presently preferred manner of activating existing metallic silver surfaces is to treat the surface with hydrogen peroxide. Preferably, the implant is immersed in the hydrogen peroxide. Suitably, 10 to 100 vols hydrogen peroxide is employed for a contact time of about 20 mins. The preference for this method is based upon convenience of use especially in view of the ready availability of hydrogen peroxide in operating theatres, where it is used to irrigate wounds at the time of operation.

The silver component can be deposited in an activated form by use of modern techniques such as sputter coating, film evaporation and ion implantation. These techniques are well known per se in the metallurgical art and hence will not be discussed in detail. Selection of a particular technique can be made from the general knowledge of the properties of the deposit produced and/or by simple experiment to assess in vitro the antimicrobial activity of the deposit.

The present invention affords many advantages over current proposals and methods of dealing with postoperative infection following implant surgery. In particular, it provides a prophylatic treatment which at least reduces the risk of postoperative infection and which can be regularly employed in implant surgery. The composite implant is self-contained requiring no energy source, such as electrical current, to produce the antimicrobial activity. Said activity is provided merely by bioerosion of the silver component. The silver ions so released are not accompanied by irritant and toxic cations such as those generated by freely dissociable salts such as silver nitrate. Further, it is less likely that the antimicrobial activity of silver ions will be circumvented by such relatively minor genetic mutation in a micro-organism as will often circumvent the antimicrobial activity of an antibiotic.

The following is a description, by way of example only and with reference to the accompanying drawings, of embodiments of the present invention. In the drawings:

FIG. 7 is a photograph of an incubated culture plate in which a silver bar was located during incubation but was subsequently removed;

FIG. 8 is a photograph of an incubated culture plate in which is located a silver bar;

Figure 1:
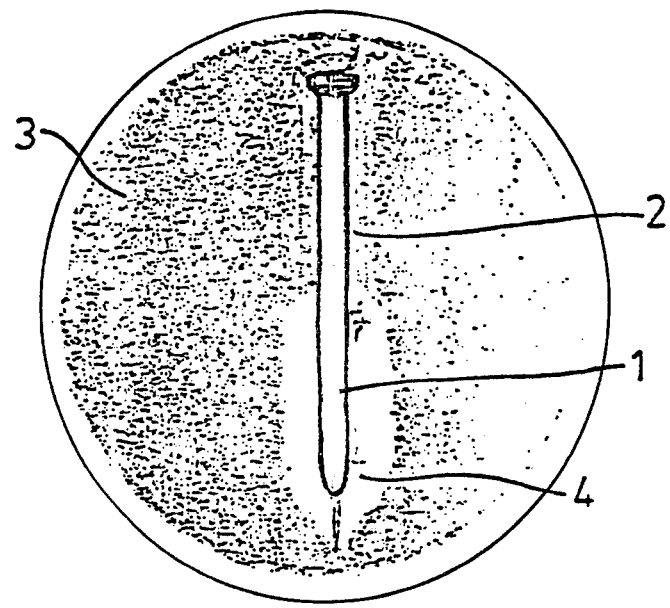
FIG. 1 is a photograph of an incubated culture plate in which is located an implant pin which is partly coated with silver.

Referring first to FIG. 1, the bottom half 1 of an implant pin 2 of titanium alloy type 318 was coated with silver by film evaporation. The thus coated pin was autoclaved in a conventional modern operating theatre autoclave with steam at about 140° C. followed by a hot air drying cycle. After cooling, it was then placed on a culture plate 3 which had been inoculated with *Staphylococcus aureus* and the culture incubated for 24 hours. As can be seen in FIG. 1, there was a clearly apparent zone 4 of inhibition around the silver coated bottom half 1 but no inhibition around the top half of the pin 2.

Figure 2:
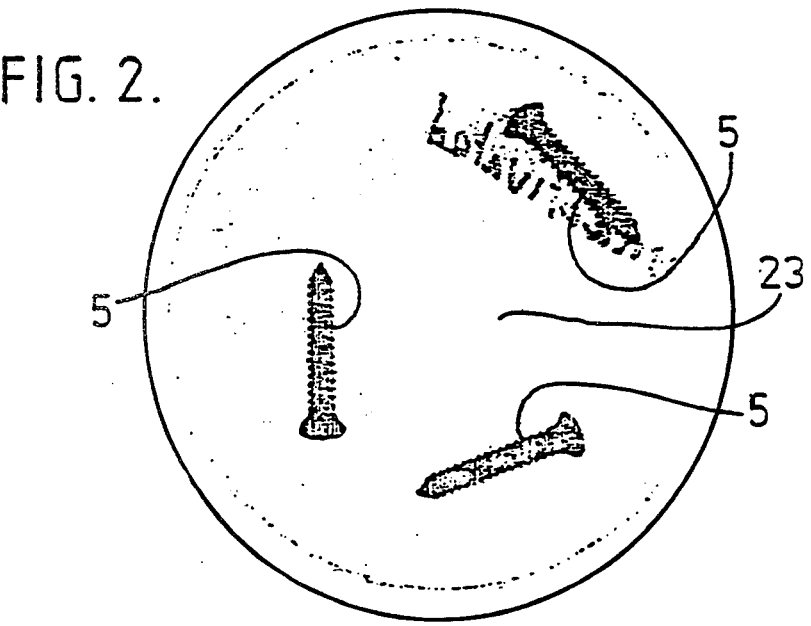
FIG. 2 is a photograph of an incubated culture plate in which are located implant screws.

Referring now to FIG. 2, three screws 5 of titanium alloy type 318 which had not been subjected to any special treatment were placed on a culture plate 23 which was inoculated and incubated as described above. As can be seen in FIG. 2, there was no inhibition of *Staph. aureus.*

Figure 3:
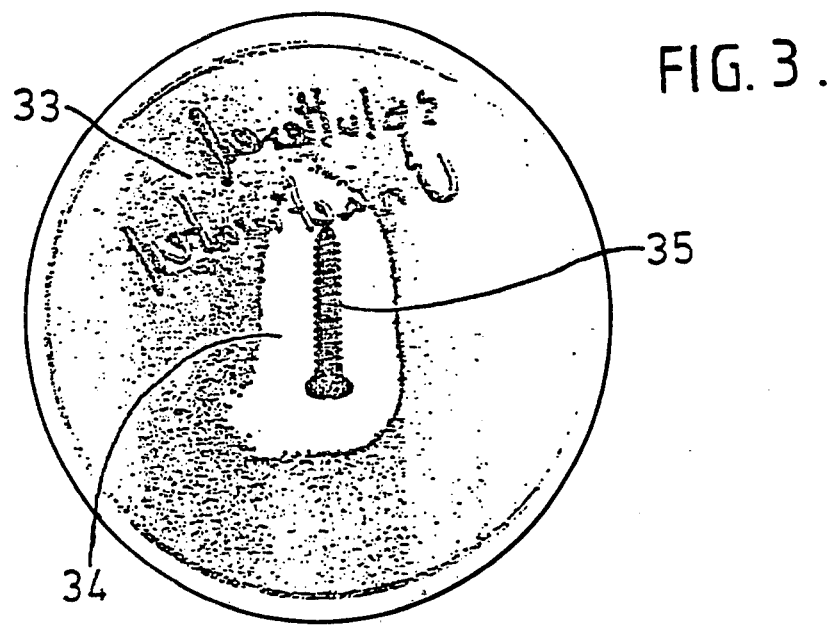
FIG. 3 is a photograph of an incubated culture plate in which is located an implant screw completely coated with silver.

A titanium alloy screw identical to the screws 5 of FIG. 2 was completely coated with a 35 nm layer of silver by sputter coating and shortly thereafter the coated screw 35 (see FIG. 3) was placed on a culture plate 33, which was inoculated and incubated as described above. As can be seen in FIG. 3, there was a clearly apparent zone 34 of inhibition completely around the silver coated screw 35.

Figure 4:
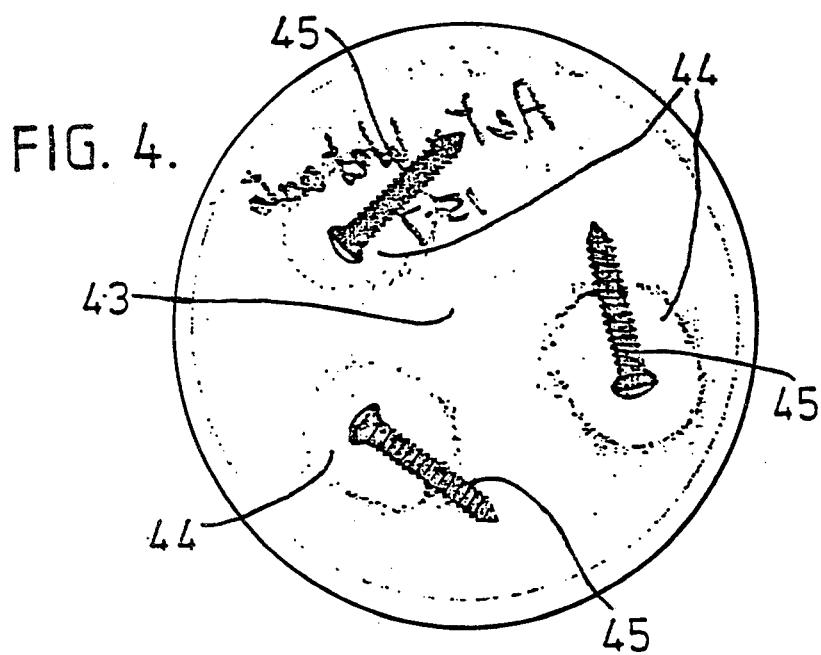
FIGS. 4, 5 and 6 are photographs of incubated culture plates in which are located implant screws which are partly coated with silver.

Three titanium alloy screws identical to the screws 5 of FIG. 2 were coated with a 35 nm layer of silver at their upper halves only by sputter coating. The partly coated screws 45 (see FIG. 4) were heated in air for 1 hour at 250° C. and then autoclaved with steam at 120° C. After cooling, the autoclaved screws 45 were placed on a culture plate 43, which was inoculated and incubated as described above. As can be seen in FIG. 4, there were clearly apparent zones 44 of inhibition around the coated upper halves of the screws 45 but no inhibition around their bottom halves.

Figure 5:
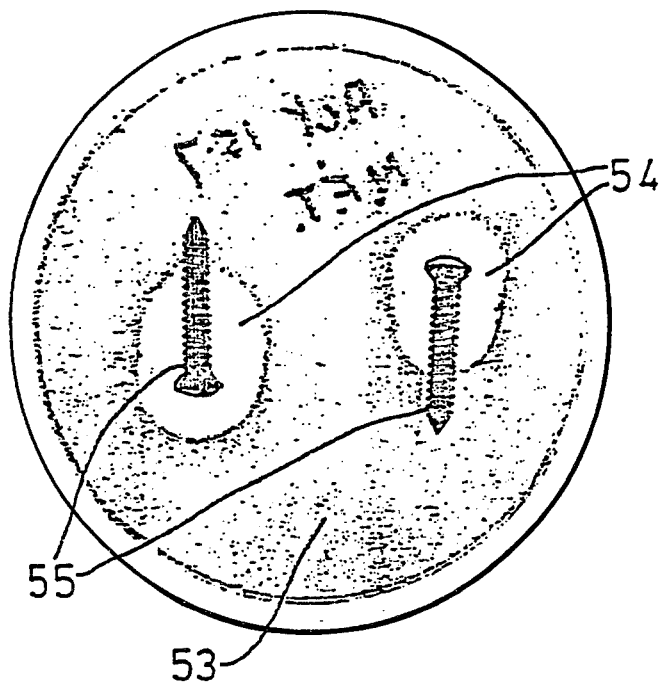

Two titanium alloy screws identical to the screws 5 of FIG. 2 were sputter coated with a 35 nm layer of silver at their upper halves only and subsequently heated in air for 1 hour at 250° C. After cooling, the partly coated screws 55 (see FIG. 5) were placed on a culture plate 53, which was inoculated and incubated as described above. As can be seen in FIG. 5, inhibition occurred only in zones 54 around the silver coated top halves of the screws 55.

Figure 6:
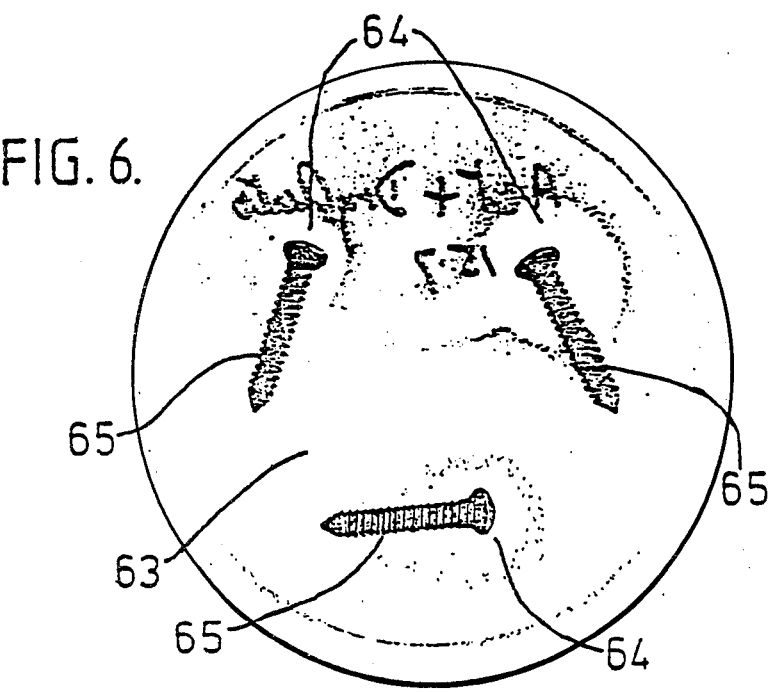

Three titanium alloy screws identical to the screws 5 of FIG. 2 were sputter coated with a 35 nm layer of silver at their upper halves only, subsequently heated in air for 1 hour at 250° C. and then autoclaved in a theatre autoclave at 140° C. with steam followed by a hot air drying cycle. After cooling, the partly coated screws 65 (see FIG. 6) were placed on a culture plate 63, which was inoculated and incubated as described above. As can be seen in FIG. 6, inhibition occurred only in zones 64 around the silver coated top halves of the screws 65.

A commercially available silver bar (99.99% purity) was heated in air at 225° C. for 1 hour and, after cooling, placed on an empty culture plate. Culture medium was poured onto the plate and then inoculated with *Staph. aureus* (top half) and *E. coli* (bottom half) and incubated as described above. As can be seen in FIG. 7, there was a clearly apparent zone of inhibition surrounding the location of the silver bar (subsequently removed) in the culture plate 73.

The procedure described above with reference to FIG. 7 was repeated except that the culture medium and bar 86 (see FIG. 8) were refrigerated for 24 hours before inoculation. As can be seen in FIG. 8, there was a clearly apparent zone 84 of inhibition in the culture plate 83 around the bar 86.

Figure 9:
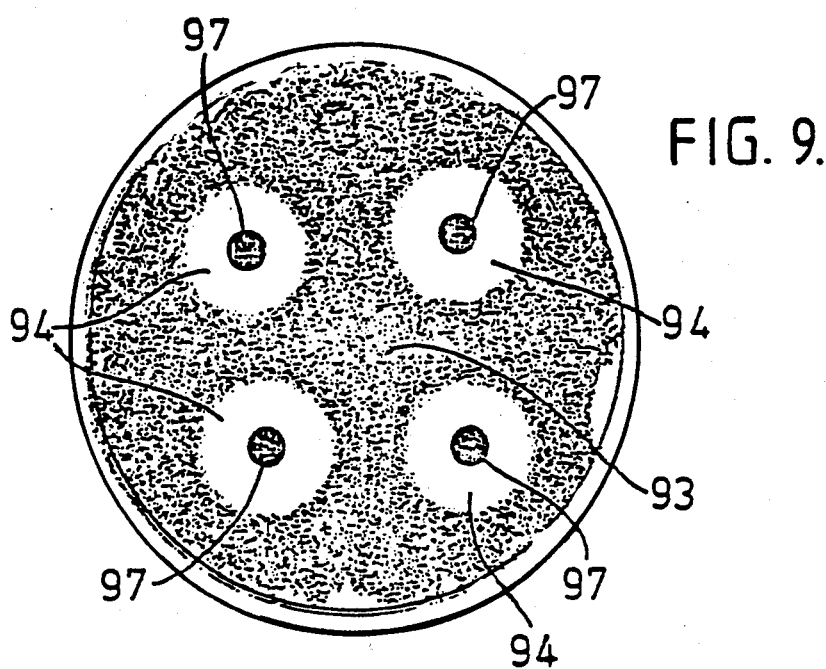
FIGS. 9, 10 and 11 are photographs of incubated culture plates in which are located silver foil discs.

Four discs of silver foil (99.99% purity) 97 (see FIG. 9) were heated at 270° C. for 20 mins in gaseous oxygen and, after cooling, placed on a culture plate 93, which was inoculated and incubated as described above. As can be seen in FIG. 9, there were clearly apparent zones 94 of inhibition surrounding the discs 97.

Figure 10:
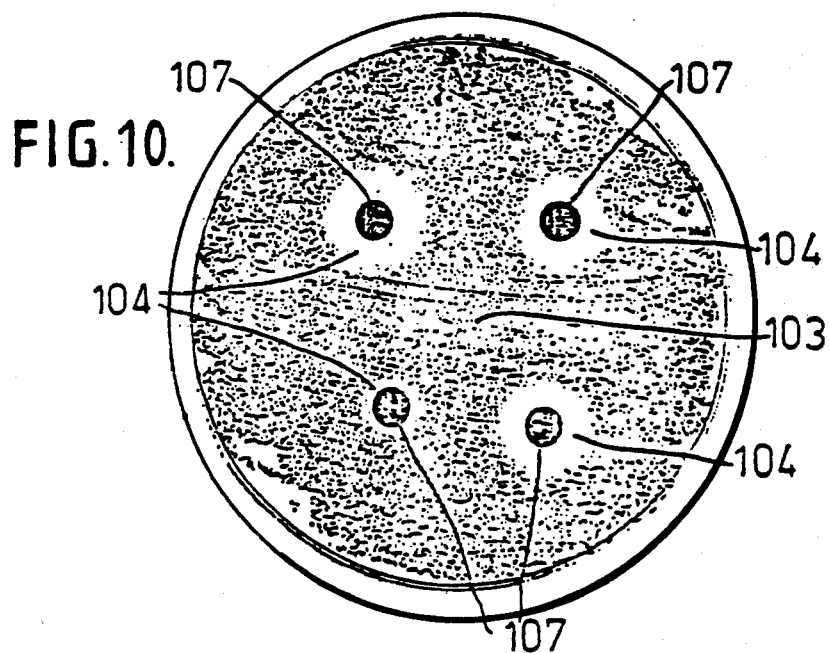

The procedure described above with reference to FIG. 9 was repeated except that the discs 107 (see FIG. 10) were heated in gaseous nitrogen instead of oxygen. As can be seen in FIG. 10, there were clearly apparent zones 104 of inhibition in the culture plate 103 surrounding the discs 101.

Figure 11:
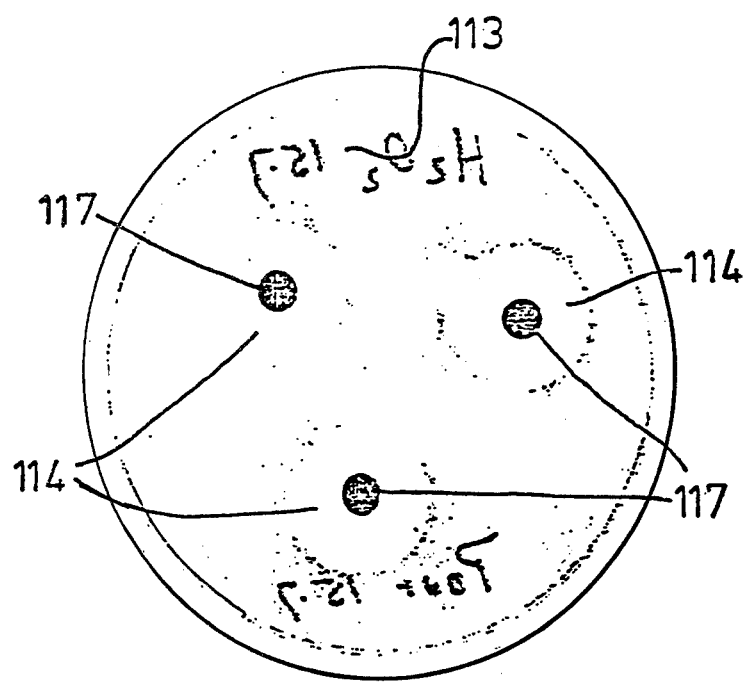

Three discs of silver foil (99.99% purity) 117 (see FIG. 11) were immersed in 100 vols hydrogen peroxide for 20 mins. The discs were thoroughly washed with water to remove all traces of hydrogen peroxide and then placed on a culture plate 113, which was inoculated and incubated as described above. As can be seen in FIG. 11, there were clearly apparent zones 114 of inhibition around the discs 113.

We claim:

1. An endoprosthetic implant comprising a permanent implant structure formed of a substantially bioinert structural material providing permanent mechanical integrity to the implant, wherein a bioerodible metallic silver component is deposited to form a surface coating 25 to 500 Angstroms in thickness on said permanent implant structure and provides in vivo a sustained release of silver ions in a concentration sufficient to provide a localized anti-microbial effect but insufficient to cause significant damage to connective tissue.

2. A surgical implant as claimed in claim 1 wherein the metallic silver is a silver alloy.

3. A surgical implant as claimed in claim 1 which is an artificial joint and the silver component is deposited at a wear surface.

4. A surgical implant as claimed in claim 1 wherein the silver component is constituted by a surface coating on at least part of the implant structure.

5. A surgical implant as claimed in claim 1 wherein the silver is deposited in or on a substrate of more readily bioerodible material.

6. A method of rendering antimicrobial an endoprosthetic implant comprising a permanent implant structure formed of a substantially bioinert structural material providing permanent mechanical integrity to the implant, said method comprising depositing on or in said implant structure coating of bioerodible metallic silver 25 to 500 Angstroms in thickness which will provide in vivo a sustained release of silver ions in a concentration sufficient to provide a localized antimicrobial effect but insufficient to cause significant damage to connective tissue.

7. A method as claimed in claim 6 wherein said tratment to activate the latently bioerodible metallic silver component comprises heating at a temperature in excess of about 180° C.

8. A method as claimed in claim 6 wherin said treatment to activate the latently bioerodible metallic silver component comprises contact with hydrogen peroxide.

9. A method as claimed in claim 6 wherein the silver is deposited as a surface coating on at least part of the permanent implant structure.

10. A method as claimed in claim 6 wherein the surgical implant is an artificial joint and the silver is deposited on or at a wear surface.

11. A method as claimed in claim 6 wherein the silver is deposited in or on a substrate of more readily bioerodible material.

12. A method as claimed in claim 6 wherein the silver is deposited by sputter coating, film evaporation or ion implantation.

13. A method of prophylactic treatment of postoperative infection following endoprosthetic implant surgery, said method comprising selecting an endoprosthetic implant comprising a permanent implant structure formed of a substantially bioinert structural material providing permanent mechanical integrity to the implant and a latently bioerodible metallic silver component deposited on a permanent implant structure to a thickness of 25 to 500 Angstroms, treating said selected insert to render the metallic silver component thereof bioerodible to provide in vivo sustained release of silver ions in a concentration sufficient to provide a localized antimicrobial effect but insufficient to cause significant damage to connective tissue, and surgically implanting the thus activated implant in the human or animal body.

14. A method as claimed in claim 13 wherein said treatment to activate the latently bioerodible metallic silver component comprises heating at a temperature in excess of about 180° C.

15. A method as claimed in claim 13 wherein said treatment to activate the latently bioerodible metallic silver component comprises contact with hydrogen peroxide.

* * * * *